(12) United States Patent
Reeder et al.

(10) Patent No.: US 7,115,747 B2
(45) Date of Patent: Oct. 3, 2006

(54) PROCESS FOR PREPARING OXAZOLE INTERMEDIATES

(75) Inventors: Michael R. Reeder, Kalamazoo, MI (US); Rick J. Imbordino, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 303 days.

(21) Appl. No.: 10/600,100

(22) Filed: Jun. 20, 2003

(65) Prior Publication Data

US 2004/0063965 A1    Apr. 1, 2004

Related U.S. Application Data

(60) Provisional application No. 60/450,478, filed on Feb. 27, 2003, provisional application No. 60/390,285, filed on Jun. 20, 2002.

(51) Int. Cl.
*C07D 263/30* (2006.01)
(52) U.S. Cl. .................................................. 548/226
(58) Field of Classification Search .............. 548/226
See application file for complete search history.

(56) References Cited

FOREIGN PATENT DOCUMENTS

| WO | WO 02/02512 A2 | 1/2002 |  |
| WO | WO 03/029169 A2 | 4/2003 |  |
| WO | WO 03/040096 A2 | 5/2003 |  |
| WO | WO 2005/049585 | * 6/2005 | ................. 548/226 |

* cited by examiner

*Primary Examiner*—Kamal A. Saeed
(74) *Attorney, Agent, or Firm*—McDonnell Boehnen Hulbert & Berghoff LLP

(57) ABSTRACT

Disclosed are compounds of formula III and a process to prepare a compound of formula III

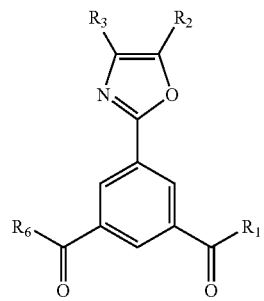

wherein $R_1$, $R_2$, $R_3$ and $R_6$ are defined herein, using a zinc chloride/optionally substituted oxazole adduct and an compound of formula I. Further disclosed are methods of using compounds of formula III to prepare compounds useful in the treatment of Alzheimer's disease and related conditions.

8 Claims, No Drawings

PROCESS FOR PREPARING OXAZOLE INTERMEDIATES

BACKGROUND OF THE INVENTION

This non-provisional application claims priority from U.S. Provisional Application Ser. No. 60/390,285 filed Jun. 20, 2002, and U.S. Provisional Application No. 60/450,478 filed Feb. 27, 2003.

FIELD OF THE INVENTION

The invention relates to processes for the preparation of oxazolyl esters which are useful in preparing pharmaceutically active compounds. The invention further comprises methods of preparing the final active compounds. The invention further comprises compounds useful in the preparation of compounds and pharmaceutical compositions to treat Alzheimer's disease and related conditions.

DESCRIPTION OF THE RELATED ART

Synthesis 583 (1996) discloses the coupling of aryl halides or aryl triflates with an oxazol-2-yl zinc chloride to provide the corresponding aryl oxazolyl. The invention provides a method for performing the coupling that unexpectedly affords improved yields and in many cases, shorter reaction times.

The methods described herein are also suitable for the preparation of compounds and/or intermediates disclosed in WO 02/02512.

SUMMARY OF INVENTION

In a first aspect, the invention provides processes for preparing compounds of formula III:

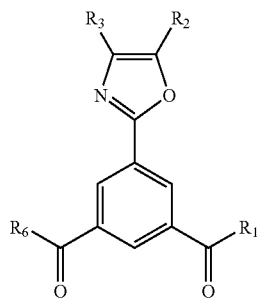

wherein:
$R_1$ is $C_1$–$C_6$ alkoxy, or $C_1$–$C_6$ alkoxyphenyl;
$R_2$ and $R_3$ are independently H; phenyl optionally substituted with $C_1$–$C_4$ alkyl, $C_1$–$C_4$ alkoxy, or dialkylamino; or $C_1$–$C_4$ alkyl; or
$R_2$ and $R_3$ and the carbons to which they are attached form a benzo ring, which is optionally substituted with $C_1$–$C_4$ alkyl, $C_1$–$C_4$ alkoxy, or dialkylamino; and
$R_6$ is $C_1$–$C_6$ alkoxy, $C_1$–$C_6$ alkoxyphenyl or $NR_4R_5$; wherein $R_4$ and $R_5$ are independently $C_1$–$C_6$ alkyl or —$C_1$–$C_6$ alkylphenyl;

comprising forming a reaction mixture comprising a compound of formula I:

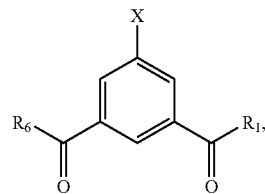

X is Br, I, OTf, or OMs;
a compound of formula II:

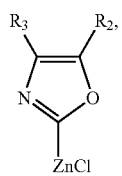

a catalyst, an optional additive, and at least one solvent.
In a second aspect, the invention provides compounds of formula III-a:

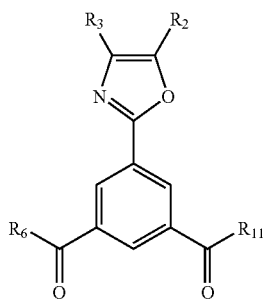

wherein:
$R_{11}$ is OH, imidazolyl, halogen, —OC(O)CH$_3$, —OC(O)C$_2$–C$_4$ alkyl, —OC(O)CF$_3$, or

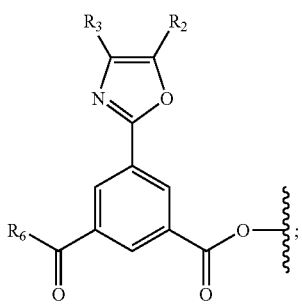

$R_2$ and $R_3$ are independently H; phenyl optionally substituted with $C_1$–$C_4$ alkyl, $C_1$–$C_4$ alkoxy, or dialkylamino; or $C_1$–$C_4$ alkyl; or
$R_2$ and $R_3$ and the carbons to which they are attached form a benzo ring, which is optionally substituted with $C_1$–$C_4$ alkyl, $C_1$–$C_4$ alkoxy, or dialkylamino; and $R_6$ is $C_1$–$C_6$ alkoxy, $C_1$–$C_6$ alkoxyphenyl, or $NR_4R_5$ where $R_4$ and $R_5$ are independently $C_1$–$C_6$ alkyl or —$C_1$–$C_6$ alkylphenyl.

Compounds of formula III-a are useful in preparing pharmaceutically active compounds. For example, the compounds of formula III-a are useful in preparing various compounds pharmaceutically active compounds disclosed in published international application WO 02/02512.

In a third aspect, the invention provides processes for preparing compounds of formula XX:

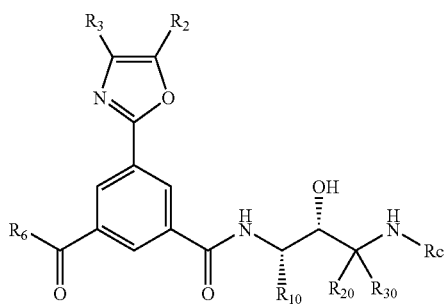

XX wherein $R_{10}$ is —$(CH_2)_{1-2}$—$S(O)_{0-2}$—$(C_1$–$C_6$ alkyl), or $C_1$–$C_{10}$ alkyl optionally substituted with 1, 2, or 3 groups independently selected from halogen, —OH, =O, —SH, —C≡N, —$CF_3$, —$C_1$–$C_3$ alkoxy, amino, mono- or dialkylamino, —N(R)C(O)R'—, —OC(=O)-amino and —OC(=O)-mono- or dialkylamino, or $C_2$–$C_6$ alkenyl or $C_2$–$C_6$ alkynyl, each of which is optionally substituted with 1, 2, or 3 groups independently selected from halogen, —OH, —SH, —C≡N, —$CF_3$, $C_1$–$C_3$ alkoxy, amino, and mono- or dialkylamino, or aryl, heteroaryl, heterocyclyl, —$C_1$–$C_6$ alkyl-aryl, —$C_1$–$C_6$ alkyl-heteroaryl, or —$C_1$–$C_6$ alkyl-heterocyclyl, where the ring portions of each are optionally substituted with 1, 2, 3, or 4 groups independently selected from halogen, —OH, —SH, —C≡N, —$NR_{105}R'_{105}$, —$CO_2R$, —N(R)COR', or —N(R)$SO_2R'$, —C(=O)—($C_1$–$C_4$) alkyl, —$SO_2$-amino, —$SO_2$-mono or dialkylamino, —C(=O)-amino, —C(=O)-mono or dialkylamino, —$SO_2$—($C_1$–$C_4$) alkyl, or $C_1$–$C_6$ alkoxy optionally substituted with 1, 2, or 3 groups which are independently selected from halogen, or $C_3$–$C_7$ cycloalkyl optionally substituted with 1, 2, or 3 groups independently selected from halogen, —OH, —SH, —C≡N, —$CF_3$, $C_1$–$C_3$ alkoxy, amino, —$C_1$–$C_6$ alkyl and mono- or dialkylamino, or $C_1$–$C_{10}$ alkyl optionally substituted with 1, 2, or 3 groups independently selected from halogen, —OH, —SH, —C≡N, —$CF_3$, —$C_1$–$C_3$ alkoxy, amino, mono- or dialkylamino and —$C_1$–$C_3$ alkyl, or $C_2$–$C_{10}$ alkenyl or $C_2$–$C_{10}$ alkynyl each of which is optionally substituted with 1, 2, or 3 groups independently selected from halogen, —OH, —SH, —C≡N, —$CF_3$, $C_1$–$C_3$ alkoxy, amino, $C_1$–$C_6$ alkyl and mono- or dialkylamino; and the heterocyclyl group is optionally further substituted with oxo;

R and R' independently are hydrogen, $C_1$–$C_{10}$ alkyl, $C_1$–$C_{10}$alkylaryl or $C_1$–$C_{10}$ alkylheteroaryl;

$R_{20}$ is selected from the group consisting of H; $C_1$–$C_6$ alkyl, optionally substituted with 1, 2, or 3 substituents that are independently selected from the group consisting of $C_1$–$C_3$ alkyl, halogen, —OH, —SH, —C≡N, —$CF_3$, $C_1$–$C_3$ alkoxy, and —$NR_{1-a}R_{1-b}$; —$(CH_2)_{0-4}$-aryl; —$(CH_2)_{0-4}$-heteroaryl; $C_2$–$C_6$ alkenyl; $C_2$–$C_6$ alkynyl; —$CONR_{N-2}R_{N-3}$; —$SO_2NR_{N-2}R_{N-3}$; —$CO_2H$; and —$CO_2$—($C_1$–$C_4$ alkyl); wherein $R_{1-a}$ and $R_{1-b}$ are independently —H or $C_1$–$C_6$ alkyl;

$R_{30}$ is selected from the group consisting of H; $C_1$–$C_6$ alkyl, optionally substituted with 1, 2, or 3 substituents independently selected from the group consisting of $C_1$–$C_3$ alkyl, halogen, —OH, —SH, —C≡N, —$CF_3$, $C_1$–$C_3$ alkoxy, and —$NR_{1-a}R_{1-b}$; —$(CH_2)_{0-4}$-aryl; —$(CH_2)_{0-4}$-heteroaryl; $C_2$–$C_6$ alkenyl; $C_2$–$C_6$ alkynyl; —CO—$NR_{N-2}R_{N-3}$; —$SO_2$—$NR_{N-2}R_{N-3}$; —$CO_2H$; and —CO—O—($C_1$–$C_4$ alkyl);

or $R_{20}$, $R_{30}$ and the carbon to which they are attached form a carbocycle of three thru seven carbon atoms, wherein one carbon atom is optionally replaced by a group selected from —O—, —S—, —$SO_2$—, or —$NR_{N-2}$—;

$R_{N-2}$ and $R_{N-3}$ at each occurrence are independently selected from the group consisting of —$C_1$–$C_8$ alkyl optionally substituted with 1, 2, or 3 groups independently selected from the group consisting of —OH, —$NH_2$, phenyl and halogen; —$C_3$–$C_8$ cycloalkyl; —($C_1$–$C_2$ alkyl)-($C_3$–$C_8$ cycloalkyl); —($C_1$–$C_6$ alkyl)—O—($C_1$–$C_3$ alkyl); —$C_2$–$C_6$ alkenyl; —$C_2$–$C_6$ alkynyl; —$C_1$–$C_6$ alkyl chain with one double bond and one triple bond; aryl; heteroaryl; heterocycloalkyl; or $R_{N-2}$, $R_{N-3}$ and the nitrogen to which they are attached form a 5, 6, or 7 membered heterocycloalkyl or heteroaryl group, wherein said heterocycloalkyl or heteroaryl group is optionally fused to a benzene, pyridine, or pyrimidine ring, and said groups are unsubstituted or substituted with 1, 2, 3, 4, or 5 groups that at each occurrence are independently $C_1$–$C_6$ alkyl, $C_1$–$C_6$ alkoxy, halogen, halo $C_1$–$C_6$ alkyl, halo $C_1$–$C_6$ alkoxy, —CN, —$NO_2$, —$NH_2$, $NH(C_1$–$C_6$ alkyl), $N(C_1$–$C_6$ alkyl) ($C_1$–$C_6$ alkyl), —OH, —$C(O)NH_2$, —$C(O)NH$ ($C_1$–$C_6$ alkyl), —$C(O)N(C_1$–$C_6$ alkyl) ($C_1$–$C_6$ alkyl), $C_1$–$C_6$ alkoxy $C_1$–$C_6$ alkyl, $C_1$–$C_6$ thioalkoxy, and $C_1$–$C_6$ thioalkoxy $C_1$–$C_6$ alkyl;

$R_C$ is hydrogen, —$(CR_{245}R_{250})_{0-4}$-aryl, —$(CR_{245}R_{250})_{0-4}$-heteroaryl, —$(CR_{245}R_{250})_{0-4}$-heterocyclyl, —$(CR_{245}R_{250})_{0-4}$-aryl-heteroaryl, —$(CR_{245}R_{250})_{0-4}$-aryl-heterocyclyl, —$(CR_{245}R_{250})_{0-4}$-aryl-aryl, —$(CR_{245}R_{250})_{0-4}$-heteroaryl-aryl, —$(CR_{245}R_{250})_{0-4}$-heteroaryl-heterocyclyl, —$(CR_{245}R_{250})_{0-4}$-heteroaryl-heteroaryl, —$(CR_{245}R_{250})_{0-4}$-heterocyclyl-heteroaryl, —$(CR_{245}R_{250})_{0-4}$-heterocyclyl-heterocyclyl, —$(CR_{245}R_{250})_{0-4}$-heterocyclyl-aryl, —$[C(R_{255})(R_{260})]_{1-3}$—CO—N—$(R_{255})_2$, —$CH(aryl)_2$, —$CH(heteroaryl)_2$, —$CH(heterocyclyl)_2$, —CH(aryl)(heteroaryl), —$(CH_2)_{0-1}$—$CH((CH_2)_{0-6}$—OH)—$(CH_2)_{0-1}$-aryl, —$(CH_2)_{0-1}$—$CH((CH_2)_{0-6}$—OH—$(CH_2)_{0-1}$-heteroaryl, —CH(-aryl or -heteroaryl) —CO—$O(C_1$–$C_4$ alkyl), —CH(—$CH_2$—OH)—CH(OH)-phenyl-$NO_2$, ($C_1$–$C_6$ alkyl)-O—($C_1$–$C_6$ alkyl)-OH; —$CH_2$—NH—$CH_2$—CH(—O—$CH_2$—$CH_3)_2$, —$(CH_2)_{0-6}$—C(=$NR_{235})(NR_{235}R_{240})$, or $C_1$–$C_{10}$ alkyl optionally substituted with 1, 2, or 3 groups independently selected from the group consisting of $R_{205}$, —OC=$ONR_{235}R_{240}$, —S (=O)_{0-2}$($C_1$–$C_6$ alkyl), —SH, —$NR_{235}C$=$ONR_{235}R_{240}$, —C=$ONR_{235}R_{240}$, and —$S(=O)_2NR_{235}R_{240}$, or —$(CH_2)_{0-3}$—$(C_3–C_8)$ cycloalkyl wherein the cycloalkyl is optionally substituted with 1, 2, or 3 groups independently selected from the group consisting of $R_{205}$, —$CO_2H$, and —$CO_2$—$(C_1–C_4$ alkyl), or cyclopentyl, cyclohexyl, or cycloheptyl ring fused to aryl, heteroaryl, or heterocyclyl wherein one, two or three carbons of the cyclopentyl, cyclohexyl, or cycloheptyl is optionally replaced with a heteroatom independently selected from NH, $NR_{215}$, O, or $S(=O)_{0-2}$, and wherein the cyclopentyl, cyclohexyl, or cycloheptyl group can be optionally substituted with one or two groups that are independently $R_{205}$, =O, —CO—$NR_{235}R_{240}$, or —$SO_2$—$(C_1–C_4$ alkyl), or $C_2–C_{10}$alkenyl or $C_2–C_{10}$alkynyl, each of which is optionally substituted with 1, 2, or 3 $R_{205}$ groups, wherein each aryl and heteroaryl is optionally substituted with 1, 2, or 3 $R_{200}$, and wherein each heterocyclyl is optionally substituted with 1, 2, 3, or 4 $R_{210}$;

$R_{200}$ at each occurrence is independently selected from —OH, —$NO_2$, halogen, —$CO_2H$, C≡N, —$(CH_2)_{0-4}$—CO—$NR_{220}R_{225}$, —$(CH_2)_{0-4}$—CO—$(C_1–C_{12}$ alkyl), —$(CH_2)_{0-4}$—CO—$(C_2–C_{12}$ alkenyl), —$(CH_2)_{0-4}$—CO—$(C_2–C_{12}$ alkynyl), —$(CH_2)_{0-4}$—CO—$(C_3–C_7$ cycloalkyl), —$(CH_2)_{0-4}$—CO-aryl, —$(CH_2)_{0-4}$—CO-heteroaryl, —$(CH_2)_{0-4}$—CO-heterocyclyl, —$(CH_2)_{0-4}$—CO—O—$R_{215}$, —$(CH_2)_{0-4}$—$SO_2$—$NR_{220}R_{225}$, —$(CH_2)_{0-4}$—SO—$(C_1–C_8$ alkyl), —$(CH_2)_{0-4}$—$SO_2$-$(C_1–C_{12}$ alkyl), —$(CH_2)_{0-4}$—$SO_2$—$(C_3–C_7$ cycloalkyl), —$(CH_2)_{0-4}$—N(H or $R_{215}$)—CO—O—$R_{215}$, —$(CH_2)_{0-4}$—N(H or $R_{215}$)—CO—$N(R_{215})_2$, —$(CH_2)_{0-4}$—N—CS—$N(R_{215})_2$, —$(CH_2)_{0-4}$—N(—H or $R_{215}$)—CO—$R_{220}$, —$(CH_2)_{0-4}$—$NR_{220}R_{225}$, —$(CH_2)_{0-4}$—O—CO—$(C_1–C_6$ alkyl), —$(CH_2)_{0-4}$—O—P(O)—$(OR_{240})_2$, —$(CH_2)_{0-4}$—O—CO—$N(R_{215})_2$, —$(CH_2)_{0-4}$—O—CS—$N(R_{215})_2$, —$(CH_2)_{0-4}$—O—$(R_{215})$, —$(CH_2)_{0-4}$—O—$(R_{215})$—COOH, —$(CH_2)_{0-4}$—S—$(R_{215})$, —$(CH_2)_{0-4}$—O—$(C_1–C_6$ alkyl optionally substituted with 1, 2, 3, or 5 —F), $C_3–C_7$ cycloalkyl, —$(CH_2)_{0-4}$—N(H or $R_{215}$)—$SO_2$—$R_{220}$, —$(CH_2)_{0-4}$—$C_3–C_7$ cycloalkyl, or $C_1–C_{10}$ alkyl optionally substituted with 1, 2, or 3 $R_{205}$ groups, or $C_2–C_{10}$ alkenyl or $C_2–C_{10}$alkynyl, each of which is optionally substituted with 1 or 2 $R_{205}$ groups, wherein the aryl and heteroaryl groups at each occurrence are optionally substituted with 1, 2, or 3 groups that are independently $R_{205}$, $R_{210}$, or $C_1–C_6$ alkyl substituted with 1, 2, or 3 groups that are independently $R_{205}$ or $R_{210}$, and wherein the heterocyclyl group at each occurrence is optionally substituted with 1, 2, or 3 groups that are independently $R_{210}$;

$R_{205}$ at each occurrence is independently selected from $C_1–C_6$ alkyl, halogen, —OH, —O-phenyl, —SH, —C≡N, —$CF_3$, $C_1–C_6$ alkoxy, $NH_2$, $NH(C_1–C_6$ alkyl) or N—$(C_1–C_6$ alkyl)($C_1–C_6$ alkyl);

$R_{210}$ at each occurrence is independently selected from halogen, $C_1–C_6$ alkoxy, $C_1–C_6$ haloalkoxy, —$NR_{220}R_{225}$, OH, C≡N, —CO—$(C_1–C_4$ alkyl), —$SO_2$—$NR_{235}R_{240}$, —CO—$NR_{235}R_{240}$, —$SO_2$—$(C_1–C_4$ alkyl), =O, or $C_1–C_6$ alkyl, $C_2–C_6$ alkenyl, $C_2–C_6$ alkynyl or $C_3–C_7$ cycloalkyl, each of which is optionally substituted with 1, 2, or 3 $R_{205}$ groups;

$R_{215}$ at each occurrence is independently selected from $C_1–C_6$ alkyl, —$(CH_2)_{0-2}$-(aryl), $C_2–C_6$ alkenyl, $C_2–C_6$ alkynyl, $C_3–C_7$ cycloalkyl, and —$(CH_2)_{0-2}$-(heteroaryl), —$(CH_2)_{0-2}$-(heterocyclyl), wherein the aryl group at each occurrence is optionally substituted with 1, 2, or 3 groups that are independently $R_{205}$ or $R_{210}$, and wherein the heterocyclyl and heteroaryl groups at each occurrence are optionally substituted with 1, 2, or 3 $R_{210}$;

$R_{220}$ and $R_{225}$ at each occurrence are independently selected from —H, —$C_3–C_7$ cycloalkyl, —$(C_1–C_2$ alkyl)-$(C_3–C_7$ cycloalkyl), —$(C_1–C_6$ alkyl)-O—$(C_1–C_3$ alkyl), —$C_2–C_6$ alkenyl, —$C_2–C_6$ alkynyl, —$C_1–C_6$ alkyl chain with one double bond and one triple bond, -aryl, -heteroaryl, and -heterocyclyl, or —$C_1–C_{10}$ alkyl optionally substituted with —OH, —$NH_2$ or halogen, wherein the aryl, heterocyclyl and heteroaryl groups at each occurrence are optionally substituted with 1, 2, or 3 $R_{270}$ groups $R_{235}$ and $R_{240}$ at each occurrence are independently H, or $C_1–C_6$ alkyl;

$R_{245}$ and $R_{250}$ at each occurrence are independently selected from —H, $C_1–C_4$ alkyl, $C_1–C_4$ alkylaryl, $C_1–C_4$ alkylheteroaryl, $C_1–C_4$ hydroxyalkyl, $C_1–C_4$ alkoxy, $C_1–C_4$ haloalkoxy, —$(CH_2)_{0-4}$—$C_3–C_7$ cycloalkyl, $C_2–C_6$ alkenyl, $C_2–C_6$ alkynyl, and phenyl; or $R_{245}$ and $R_{250}$ are taken together with the carbon to which they are attached to form a carbocycle of 3, 4, 5, 6, or 7 carbon atoms, where one carbon atom is optionally replaced by a heteroatom selected from —O—, —S—, —$SO_2$—, and —$NR_{220}$—;

$R_{255}$ and $R_{260}$ at each occurrence are independently selected from —H, —$(CH_2)_{1-2}$—$S(O)_{0-2}$—$(C_1–C_6$ alkyl), —$(C_1–C_4$ alkyl)-aryl, —$(C_1–C_4$ alkyl)-heteroaryl, —$(C_1–C_4$ alkyl)-heterocyclyl, -aryl, -heteroaryl, -heterocyclyl, —$(CH_2)_{1-4}$—$R_{265}$—$(CH_2)_{0-4}$-aryl, —$(CH_2)_{1-4}$—$R_{265}$—$(CH_2)_{0-4}$-heteroaryl, —$(CH_2)_{1-4}$—$R_{265}$—$(CH_2)_{0-4}$-heterocyclyl, or $C_1–C_6$ alkyl, $C_2–C_6$ alkenyl, $C_2–C_6$ alkynyl or —$(CH_2)_{0-4}$—$C_3–C_7$ cycloalkyl, each of which is optionally substituted with 1, 2, or 3 $R_{205}$ groups, wherein each aryl or phenyl is optionally substituted with 1, 2, or 3 groups that are independently $R_{205}$, $R_{210}$, or $C_1–C_6$ alkyl substituted with 1, 2, or 3 groups that are independently $R_{205}$ or $R_{210}$, and wherein each heterocyclyl is optionally substituted with 1, 2, 3, or 4 $R_{210}$;

$R_{265}$ at each occurrence is independently —O—, —S— or —N($C_1–C_6$ alkyl)-;

$R_{270}$ at each occurrence is independently $R_{205}$, halogen $C_1–C_6$ alkoxy, $C_1–C_6$ haloalkoxy, $NR_{235}R_{240}$, —OH, —C≡N, —CO—$(C_1–C_4$ alkyl), —$SO_2$—$NR_{235}R_{240}$, —CO—$NR_{235}R_{240}$, —$SO_2$—$(C_1–C_4$ alkyl), =O, or $C_1–C_6$ alkyl, $C_2–C_6$ alkenyl, $C_2–C_6$ alkynyl or —$(CH_2)_{0-4}$—$C_3–C_7$ cycloalkyl, each of which is optionally substituted with 1, 2, or 3 $R_{205}$ groups;

comprising forming a reaction mixture comprising a compound of formula III-a

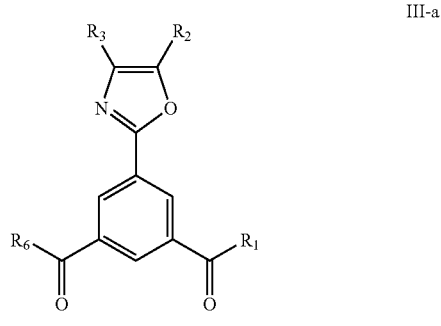

III-a wherein
$R_1$ is OH, imidazolyl, halogen, —OC(O)CH$_3$, —OC(O)CF$_3$, or

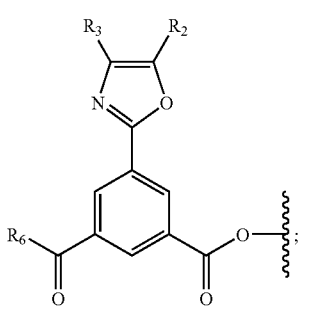

$R_2$ and $R_3$ are independently H, phenyl, or $C_1$–$C_4$ alkyl; or
$R_2$ and $R_3$ and the carbons to which they are attached form a benzo ring which is optionally substituted with $C_1$–$C_4$ alkyl, $C_1$–$C_4$ alkoxy, or dialkylamino; and
$R_6$ is $C_1$–$C_6$ alkoxy or NR$_4$R$_5$; wherein
$R_4$ and $R_5$ are independently $C_1$–$C_6$ alkyl;
and a compound of formula VIII

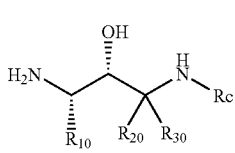

VIII in a solvent with an optional base and an optional additive, such as, for example, a ligand for the catalyst used in the formulation of compounds of formula I.

Compounds of formula VIII can be prepared, for example, as according to procedures described in published international application WO 02/02512.

In still another aspect, the invention provides a process for converting compounds of formula III into compounds of formula III-a.

In yet another aspect, the invention provides compound of formula III-a:

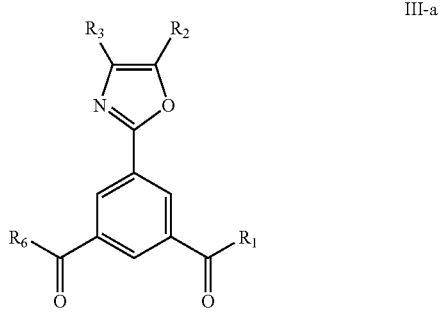

III-a wherein
$R_1$ is OH, imidazolyl, halogen, —OC(O)CH$_3$, —OC(O)CF$_3$, or

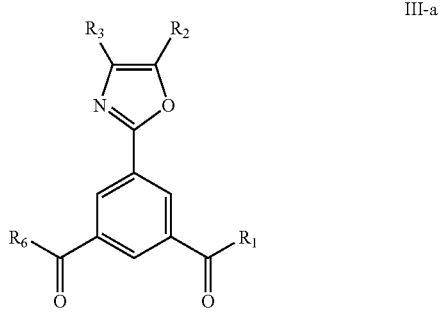

$R_2$ and $R_3$ are independently H, phenyl, or $C_1$–$C_4$ alkyl; or
$R_2$ and $R_3$ and the carbons to which they are attached form a benzo ring which is optionally substituted with $C_1$–$C_4$ alkyl, $C_1$–$C_4$ alkoxy, or dialkylamino; and
$R_6$ is $C_1$–$C_6$ alkoxy or NR$_4$R$_5$; wherein
$R_4$ and $R_5$ are independently $C_1$–$C_6$ alkyl.

The compounds of Formula III-a are useful in preparing the pharmaceutically active compounds disclosed in WO 02/02512.

In another aspect, the invention provides a process for the preparation of the zinc chloride/oxazole adduct of formula II.

DETAILED DESCRIPTION OF THE INVENTION

As noted above, in one aspect, the invention provides methods of preparing compounds of formula III using compounds of formula II.

In a preferred method for preparing compounds of formula III using compounds of formula II, the catalyst is a transition metal catalyst. More preferably, it is a Pt or Pd catalyst. Even more preferably, it is a Pd(0) catalyst.

Still more preferably, the catalyst is Pd(PPh$_3$)$_4$, PdCl$_2$(PPh$_3$)$_2$, PdCl$_2$, PdCl$_2$ and PPh$_3$, or Pd(OCOCH$_3$)$_2$. Most preferably the catalyst is Pd(PPh$_3$)$_4$.

In a preferred method the reaction is carried out in a solvent. More preferably, the method is carried out in at least one polar, aprotic solvent. Still more preferably, the solvent is tetrahydrofuran, tetramethyltetrahydrofuran, glyme, methyl t-butyl ether, or mixtures thereof. Even more preferably, the solvent is tetrahydrofuran.

In a preferred method the reaction is carried out at a temperature of from about 25° C. to about the refluxing temperature of the solvent used. More preferably, the temperature is about 30° C. to about 75° C. Even more preferably, the temperature is about 40° C. to about 60° C. Still more preferably, the temperature is 45–55° C.

All of the reagents can preferably be combined at once, i.e., at nearly the same time, or within a short time of each other. In an alternative method, the reaction mixture is formed by combining the compound of formula I, the compound of formula II, the catalyst and any additional additive (if necessary) over a period of about 0.5 hours to about 4 hours, wherein this period is also known as the addition time. More preferably, the addition time is about 1 hour to about 3 hours. Even more preferably, the addition time is about 1.5 hours to about 2.5 hours. Most preferably it is 2 hours. It should be noted that the compound of formula I may be added to a mixture containing the compound of formula II, or vice versa.

For example, the compound of formula II can be added to the reaction mixture, e.g. a solution, comprising the compound of formula I and the catalyst. Or, the compound of formula I, and the catalyst, can be added to the reaction mixture, e.g. a solution, comprising the compound of formula II.

In a preferred method the transition metal catalyst is present in 0.01 to 20 mole percent, based on the amount of the compound of formula I. More preferably the catalyst is present in 0.1 to 10 mole percent, based on the amount of the compound of formula I. Even more preferably, the catalyst is present in 1 to 7 mole percent, based on the amount of the compound of formula I.

In a preferred method, after all of the compounds and reagents have been combined, thereby forming the reaction mixture, the reaction mixture is heated at the temperatures mentioned above for about 0.5 to about 24 hours. More preferably, the reaction mixture is heated for about 0.5 to about 4 hours. Even more preferably, the reaction mixture is heated for about 0.5 to about 2.25 hours.

In a preferred method, the compound of formula II is used in an excess from 1.001 to 10 equivalents, based on the amount of compound of formula I. Preferably, the compound of formula II is used in an excess from 1.01 to 5 equivalents, based on the amount of compound of formula I. Even more preferably, the compound of formula II is used in an excess from 1.05 to 4 equivalents, based on the amount of compound of formula I. Still more preferably, the second compound is used in an excess from 1.1 to 1.7 equivalents, based on the amount of compound of formula I. In a most preferred embodiment, about 3 equivalents are utilized.

In a preferred method of preparing compounds of formula III,

X is Br;

$R_2$ and $R_3$ are independently H, methyl or ethyl;

$R_6$ is $NR_4R_5$ where $R_4$ and $R_5$ are both $C_3$ alkyl; and $R_1$ is $C_1-C_4$ alkyl.

In this aspect, $R_1$ is more preferably methyl or ethyl.

In another aspect, the invention provides an improved method for preparing the zinc chloride/oxazole adduct of formula II.

In a preferred aspect, the compound of formula II is prepared using solid $ZnCl_2$. Preferably, 1.1 to about 10 equivalents of $ZnCl_2$ based on the amount of the particular oxazole used is used to prepare the compound of formula II. More preferably, 1.1 to about 5 equivalents of $ZnCl_2$ is used. Even more preferably, about 2.5 to about 3.5 equivalents of $ZnCl_2$ is used.

Preferred compounds of formula III and formula III-a include compounds wherein $R_2$ and $R_3$ are independently H, methyl, or phenyl; or $R_2$, $R_3$ and the carbons to which they are attached form a benzo ring. More preferably, $R_2$ and $R_3$ are independently H or methyl. Even more preferably, $R_2$ and $R_3$ are both H.

More preferred compounds of formula III and formula III-a include compounds wherein $R_6$ is $NR_4R_5$ where $R_4$ and $R_5$ are both $C_3$ alkyl or $R_4$ and $R_5$ are independently $C_1-C_4$ alkyl or benzyl. Preferably, $R_4$ and $R_5$ are both $C_3$ alkyl. Alternatively, $R_4$ and $R_5$ are independently $C_1-C_4$ alkyl or benzyl.

Even more preferred compounds of formula III-a include compounds wherein $R_6$ is $NR_4R_5$ where $R_4$ and $R_5$ are both $C_3$ alkyl or $R_4$ and $R_5$ are independently $C_1-C_4$ alkyl or benzyl. Preferably $R_4$ and $R_5$ are both $C_3$ alkyl. Alternatively, $R_4$ and $R_5$ are independently $C_1-C_4$ alkyl or benzyl; and $R_1$ is OH.

Even more preferred compounds of formula III include compounds wherein $R_6$ is $NR_4R_5$ wherein $R_4$ and $R_5$ are both $C_3$ alkyl or $R_4$ and $R_5$ are independently $C_1-C_4$ alkyl or benzyl. Preferably $R_4$ and $R_5$ are both $C_3$ alkyl. Alternatively, $R_4$ and $R_5$ are independently $C_1-C_4$ alkyl or benzyl; and $R_1$ is $C_1-C_4$ alkoxy, more preferably $R_1$ is methyl or ethyl. Even more preferably, $R_1$ is methyl.

Even more preferred compounds of formula III-a include compounds wherein $R_6$ is $NR_4R_5$ where $R_4$ and $R_5$ are both $C_3$ alkyl or $R_4$ and $R_5$ are independently $C_1-C_4$ alkyl or benzyl. Preferably $R_4$ and $R_5$ are both C3 alkyl. Alternatively, $R_4$ and $R_5$ are independently $C_1-C_4$ alkyl or benzyl; and $R_1$ is halogen, more preferably $R_1$ is chloro.

Even more preferred compounds of formula III-a include compounds wherein $R_6$ is $NR_4R_5$; wherein $R_4$ and $R_5$ are both $C_3$ alkyl or $R_4$ and $R_5$ are independently $C_1-C_4$ alkyl or benzyl.

Preferably $R_4$ and $R_5$ are both $C_3$ alkyl. Alternatively, $R_4$ and $R_5$ are independently $C_1-C_4$ alkyl or benzyl; and $R_1$ is

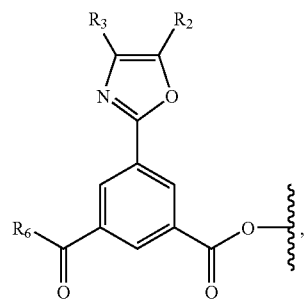

—OC(O)CH$_3$, or —OC(O)CF$_3$.

In another aspect, preferred compounds of formula III and formula III-a are those compounds wherein $R_6$ is $C_1-C_6$ alkoxy or $C_1-C_6$ alkoxyphenyl, more preferably $R_6$ is $C_1-C_4$ alkoxy or benzyloxy. Still more preferably, $R_6$ is methoxy or ethoxy. Even more preferably, $R_6$ is methoxy.

Other preferred compounds of formula III-a include those where $R_2$ and $R_3$ are independently H, phenyl, or $C_1$–$C_4$ alkyl; or $R_2$ and $R_3$ and the carbons to which they are attached form a benzene ring which is optionally substituted with $C_1$–$C_4$ alkyl, $C_1$–$C_4$ alkoxy, or dialkylamino; and $R_6$ is $C_1$–$C_6$ alkoxy or $NR_4R_5$; wherein $R_4$ and $R_5$ are independently $C_1$–$C_6$ alkyl;

Still other preferred compounds of formula III-a include those compounds wherein $R_2$ and $R_3$ are independently H, phenyl, or $C_1$–$C_4$ alkyl.

Other preferred compounds of formula III-a are those wherein $R_6$ is $NR_4R_5$ wherein $R_4$ and $R_5$ are $C_1$–$C_6$ alkyl.

Still other preferred compounds of formula III-a are those wherein $R_2$ and $R_3$ are independently H, phenyl, or $C_1$–$C_4$ alkyl; and $R_6$ is $NR_4R_5$; wherein $R_4$ and $R_5$ are $C_1$–$C_6$ alkyl.

Still other preferred compounds of formula III-a are those wherein $R_1$ is OH.

Still other preferred compounds of formula III-a are those wherein $R_1$ is OH; and $R_2$ and $R_3$ are independently H, phenyl, or $C_1$–$C_4$ alkyl. More preferably when $R_1$ is OH, $R_2$ and $R_3$ are independently H, methyl or ethyl. Also preferred when $R_1$ is OH are compounds wherein $R_2$ and $R_3$ are independently H or phenyl.

Still other preferred compounds of formula III-a are those wherein $R_1$ is OH; and $R_2$ and $R_3$ are independently H, phenyl, or $C_1$–$C_4$ alkyl. More preferably $R_2$ and $R_3$ are independently H, methyl or ethyl. Also preferred are the compounds wherein $R_2$ and $R_3$ are independently H or phenyl; and $R_6$ is $NR_4R_5$; wherein $R_4$ and $R_5$ are $C_1$–$C_6$ alkyl. More preferably, $R_4$ and $R_5$ are both $C_3$ alkyl. Also preferred is when $R_4$ and $R_5$ are both $C_2$ alkyl. Also preferred is when $R_4$ and $R_5$ are both $C_4$ alkyl.

As noted above, the invention provides a process for preparing a compound of formula XX.

In one aspect, the process for preparing compounds of formula XX is carried out in a solvent. Preferably, the solvent is THF, DMF, $CH_2Cl_2$, $CHCl_3$, or a mixture thereof. Useful co-solvents include hexanes, heptane, n-methylpyrrolidine, trifluoroethane, tetramethyltetrahydrofuran, and cyclohexane.

The optional base is typically an amine, preferably a tertiary amine. Examples of suitable amine bases are selected from pyridine, collidine, di-tertiarybutyl pyridine, triethylamine, diisopropylethylamine, dimethylamino pyridine, lutidine and mixtures thereof.

The optional additive is typically am amide coupling agent. Examples of suitable amide coupling agents are 1, 2, or 3 of the following 1-(3-dimethylaminopropyl)-3-ethyl-carbodiimide hydrochloride (also known as EDC and/or EDCI), 1-hydroxybenzotriazole hydrate (HOBT), benzotriazole, 1-hydroxy-7-azabenzotriazole (HOAT), O-(7-azabenzotriazol-1-yl)-N,N,N',N',-tetramethyluronium hexafluorophosphate (HATU), O-benzotriazol-1-yl-N,N,N',N'-tetramethyluronium hexafluorophosphate (HBTU), PYBop, Bop, BopCl, or 1,3-dicyclohexylcarbodiimide (DCC).

The reaction is preferably carried out for about 0.5 to about 24 hours. More preferred reaction times are about 2 hours to about 16 hours.

Preferably, the reaction is carried out a temperature of about −5° C. to about 70° C. More preferably at a temperature of about 0° C. to about 50° C. Even more preferably, at a temperature of about 15° C. to about 40° C. Still more preferably at a temperature of about 20° C. to about 40° C.

In another aspect, the compound of formula III-a is used in excess, based on the amount of the compound of formula VIII. Preferably about 1.01 to about 5 equivalents of the compound of formula III-a are used. More preferably, from about 1.1 to about 3 equivalents of the compound of formula III-a are used.

In another aspect, when the optional base is present, it is used 1) catalytically, 2) in a one to one ratio based on the amount of the compound of formula III-a, or 3) in excess. If used catalytically about 0.01 to about 0.99 equivalents based on the amount of the compound of formula III-a can be used. If used in excess, there are 1.0001 to about 30 equivalents of base are used. More preferably, 1.001 to about 20 equivalents of base are used. Still more preferably, 1.01 to about 10 equivalents of base are used. More preferably, 1.1 to about 5 equivalents of base are used. However, one skilled in the art will recognize that the exact amount of base (or even substituting a different base) may be varied without deviating from the scope of the invention.

If any of the additives are added, one skilled in the art will recognize the appropriate amount of the additive that should be added. The use of such reagents is known in the art of organic synthesis and medicinal chemistry. It is also known in the art of peptide synthesis and amide couplings.

Definitions

By "alkyl" and "$C_1$–$C_6$ alkyl" in the present invention is meant straight or branched chain alkyl groups having 1–6 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. It is understood that in cases where an alkyl chain of a substituent (e.g. of an alkyl, alkoxy or alkenyl group) is shorter or longer than 6 carbons, it will be so indicated in the second "C" as, for example, "$C_1$–$C_{10}$" indicates a maximum of 10 carbons.

By "alkoxy" and "$C_1$–$C_6$ alkoxy" in the present invention is meant straight or branched chain alkyl groups having 1–6 carbon atoms, attached through at least one divalent oxygen atom, such as, for example, methoxy, ethoxy, propoxy, isopropoxy, n-butoxy, sec-butoxy, tert-butoxy, pentoxy, isopentoxy, neopentoxy, hexoxy, and 3-methylpentoxy.

By the term "halogen" in the present invention is meant fluorine, bromine, chlorine, and iodine.

By the term, "OTf" is meant —$OSO_2CF_3$.

By the term, "OMs" is meant —$OSO_2CH_3$.

By the term "halogen" in the present invention is meant fluorine, bromine, chlorine, and/or iodine.

"Alkenyl" and "$C_2$–$C_6$ alkenyl" means straight and branched hydrocarbon radicals having from 2 to 6 carbon atoms and from one to three double bonds and includes, for example, ethenyl, propenyl, 1-but-3-enyl, 1-pent-3-enyl, 1-hex-5-enyl and the like.

"Alkynyl" and "$C_2$–$C_6$ alkynyl" means straight and branched hydrocarbon radicals having from 2 to 6 carbon atoms and one or two triple bonds and includes ethynyl, propynyl, butynyl, pentyn-2-yl and the like.

As used herein, the term "cycloalkyl" refers to saturated carbocyclic radicals having three to twelve carbon atoms. The cycloalkyl can be monocyclic, or a polycyclic fused system. Examples of such radicals include cyclopropyl, cyclobutyl, cyclopentyl and cyclohexyl. Preferred cycloalkyl groups are cyclopentyl, cyclohexyl, and cycloheptyl. The cycloalkyl groups herein are unsubstituted or, as specified, substituted in one or more substitutable positions with various groups. For example, such cycloalkyl groups may be optionally substituted with, for example, $C_1$–$C_6$ alkyl, $C_1$–$C_6$ alkoxy, halogen, hydroxy, cyano, nitro, amino, mono($C_1$–$C_6$)alkylamino, di($C_1$–$C_6$)alkylamino, $C_2$–$C_6$alkenyl, $C_2$–$C_6$alkynyl, $C_1$–$C_6$ haloalkyl, $C_1$–$C_6$ haloalkoxy, amino($C_1$–$C_6$)alkyl, mono($C_1$–$C_6$)alkylamino ($C_1$–$C_6$)alkyl or di($C_1$–$C_6$)alkylamino($C_1$–$C_6$)alkyl.

By "aryl" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl), which is optionally mono-, di-, or trisubstituted. Preferred aryl groups of the present invention are phenyl, 1-naphthyl, 2-naphthyl, indanyl, indenyl, dihydronaphthyl, tetralinyl or 6,7,8,9-tetrahydro-5H-benzo[a]cycloheptenyl. The aryl groups herein are unsubstituted or, as specified, substituted in one or more substitutable positions with various groups. For example, such aryl groups may be optionally substituted with, for example, $C_1$–$C_6$ alkyl, $C_1$–$C_6$ alkoxy, halogen, hydroxy, cyano, nitro, amino, mono($C_1$–$C_6$)alkylamino, di($C_1$–$C_6$) alkylamino, $C_2$–$C_6$alkenyl, $C_2$–$C_6$alkynyl, $C_1$–$C_6$ haloalkyl, $C_1$–$C_6$ haloalkoxy, amino($C_1$–$C_6$)alkyl, mono($C_1$–$C_6$)alkylamino($C_1$–$C_6$)alkyl or di($C_1$–$C_6$) alkylamino ($C_1$–$C_6$) alkyl.

By "heteroaryl" is meant one or more aromatic ring systems of 5-, 6-, or 7-membered rings which includes fused ring systems of 9–11 atoms containing at least one and up to four heteroatoms selected from nitrogen, oxygen, or sulfur. Preferred heteroaryl groups of the present invention include pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. The heteroaryl groups herein are unsubstituted or, as specified, substituted in one or more substitutable positions with various groups. For example, such heteroaryl groups may be optionally substituted with, for example, $C_1$–$C_6$ alkyl, $C_1$–$C_6$ alkoxy, halogen, hydroxy, cyano, nitro, amino, mono($C_1$–$C_6$)alkylamino, di($C_1$–$C_6$)alkylamino, $C_2$–$C_6$alkenyl, $C_2$–$C_6$alkynyl, $C_1$–$C_6$ haloalkyl, $C_1$–$C_6$ haloalkoxy, amino($C_1$–$C_6$)alkyl, mono($C_1$–$C_6$)alkylamino($C_1$–$C_6$)alkyl or di($C_1$–$C_6$) alkylamino ($C_1$–$C_6$) alkyl.

By "heterocycle", "heterocycloalkyl" or "heterocyclyl" is meant one or more carbocyclic ring systems of 4-, 5-, 6-, or 7-membered rings which includes fused ring systems of 9–11 atoms containing at least one and up to four heteroatoms selected from nitrogen, oxygen, or sulfur. Preferred heterocycles of the present invention include morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl S-oxide, tetrahydrothienyl S,S-dioxide and homothiomorpholinyl S-oxide. The heterocycle groups herein are unsubstituted or, as specified, substituted in one or more substitutable positions with various groups. For example, such heterocycle groups may be optionally substituted with, for example, $C_1$–$C_6$ alkyl, $C_1$–$C_6$ alkoxy, halogen, hydroxy, cyano, nitro, amino, mono($C_1$–$C_6$)alkylamino, di ($C_1$–$C_6$)alkylamino, $C_2$–$C_6$ alkenyl, $C_2$–$C_6$alkynyl, $C_1$–$C_6$ haloalkyl, $C_1$–$C_6$ haloalkoxy, amino($C_1$–$C_6$)alkyl, mono($C_1$–$C_6$)alkylamino ($C_1$–$C_6$)alkyl, di($C_1$–$C_6$)alkylamino($C_1$–$C_6$)alkyl or =O.

The invention provides methods of converting compounds of formula III into compounds of formula III-a. Such methods are outlined in schemes B and C (wherein $X_1$ is as defined below) and are discussed in more detail below. Methods for converting an ester into an amide are well known in the art. Such methods include, for example, base hydrolysis using LiOH, NaOH, or KOH as the base, or acid hydrolysis using HCl, $H_2SO_4$, $H_3PO_4$, triflic acid, para-toluene sulfonic acid, or $HNO_3$. The invention also contemplates the use of two or more acids in combination or two or more bases in combination to effect the hydrolysis. Other methods will be readily apparent to one of skill in the art.

The conversion of the acid into the acid chloride is preferably accomplished by using $SOCl_2$, $SO_2Cl_2$, or oxalyl chloride. Other reagents known in the art can be conveniently used to effect this transformation.

The conversion of the acid into the imidazolyl compound is preferably carried out using carbonyl diimidazole (CDI.)

The conversion of the acid into an acid anhydride is accomplished by treating the acid with another acid anhydride, such as acetic anhydride (thereby forming a mixed anhydride), or the conversion can be effected by dehydrating two acid molecules through the use of heat or another dehydrating agent. Treatment with an acid anhydride is more preferable. On an industrial scale, heating is one preferred method of preparing the anhydride.

The processes of the invention are outlined in the following Schemes.
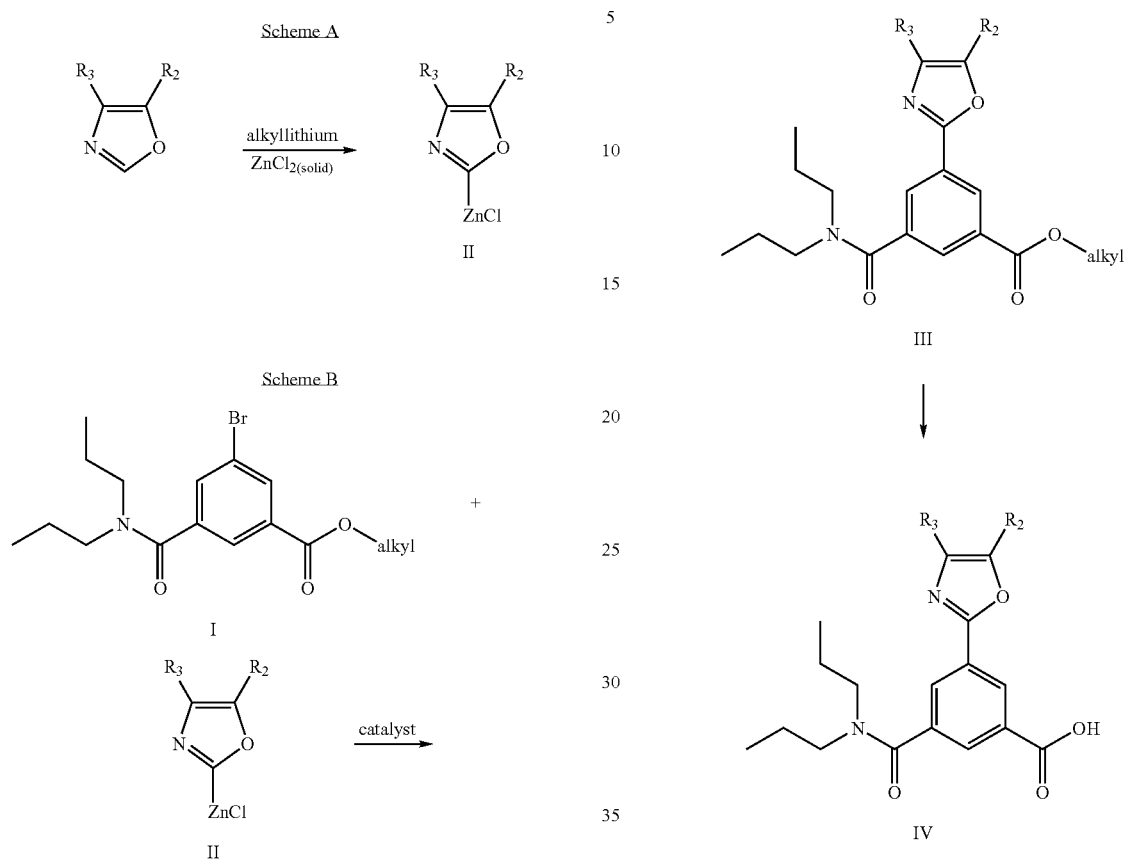
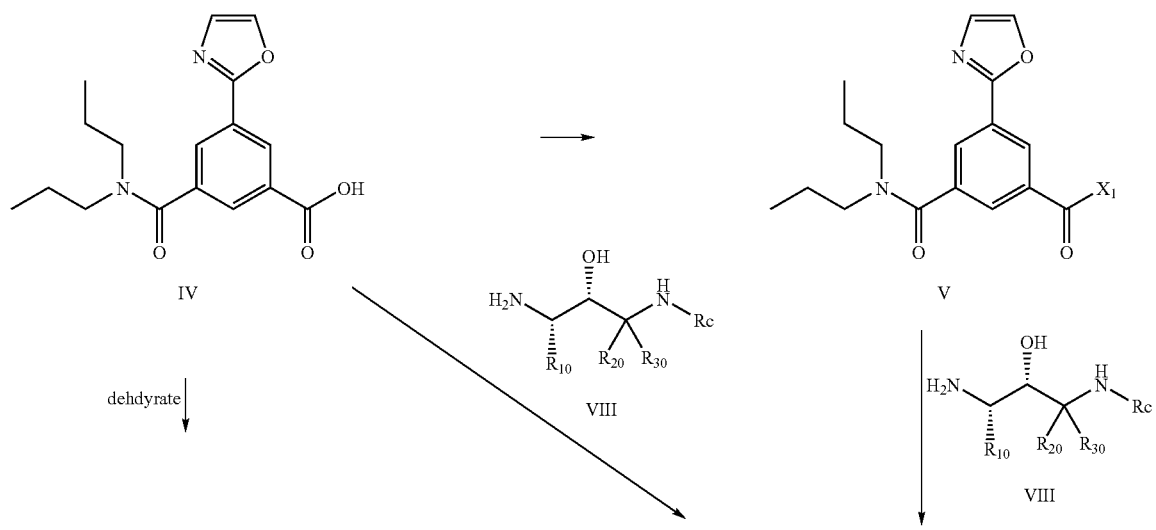

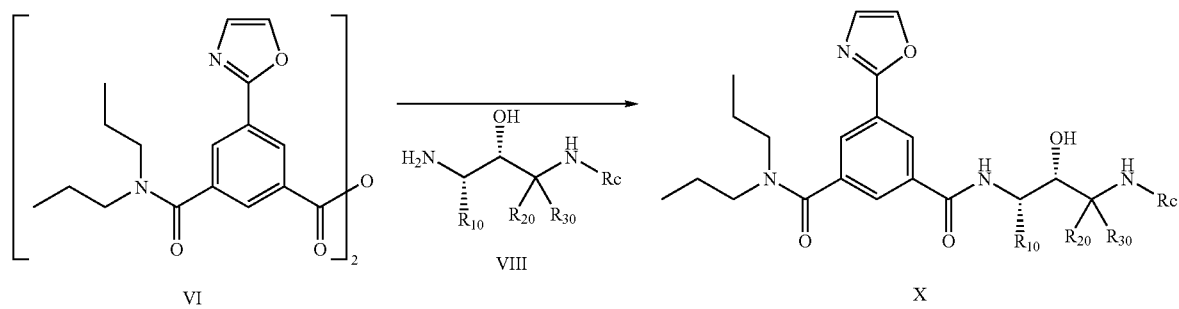
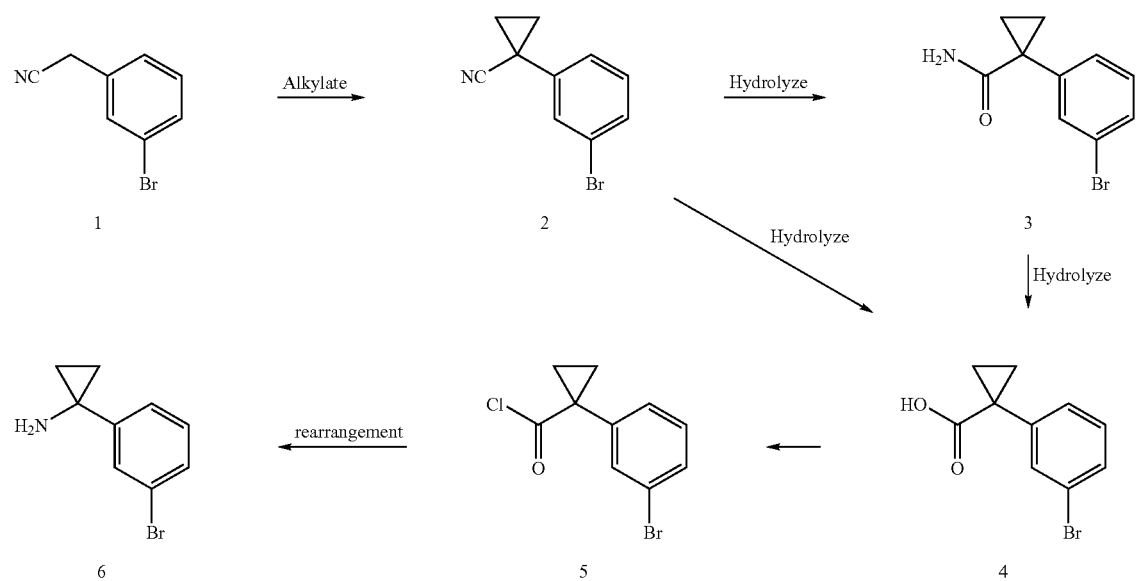
Scheme D
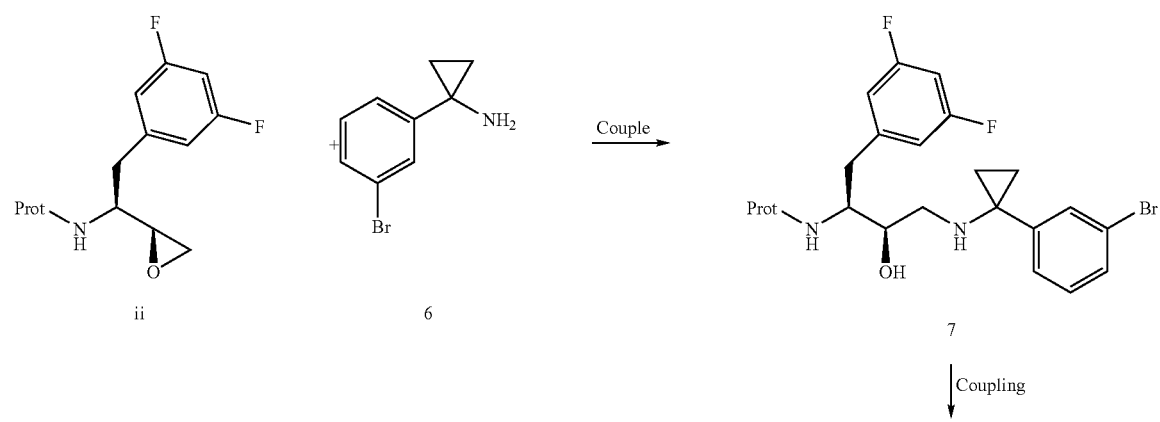
Scheme E

-continued
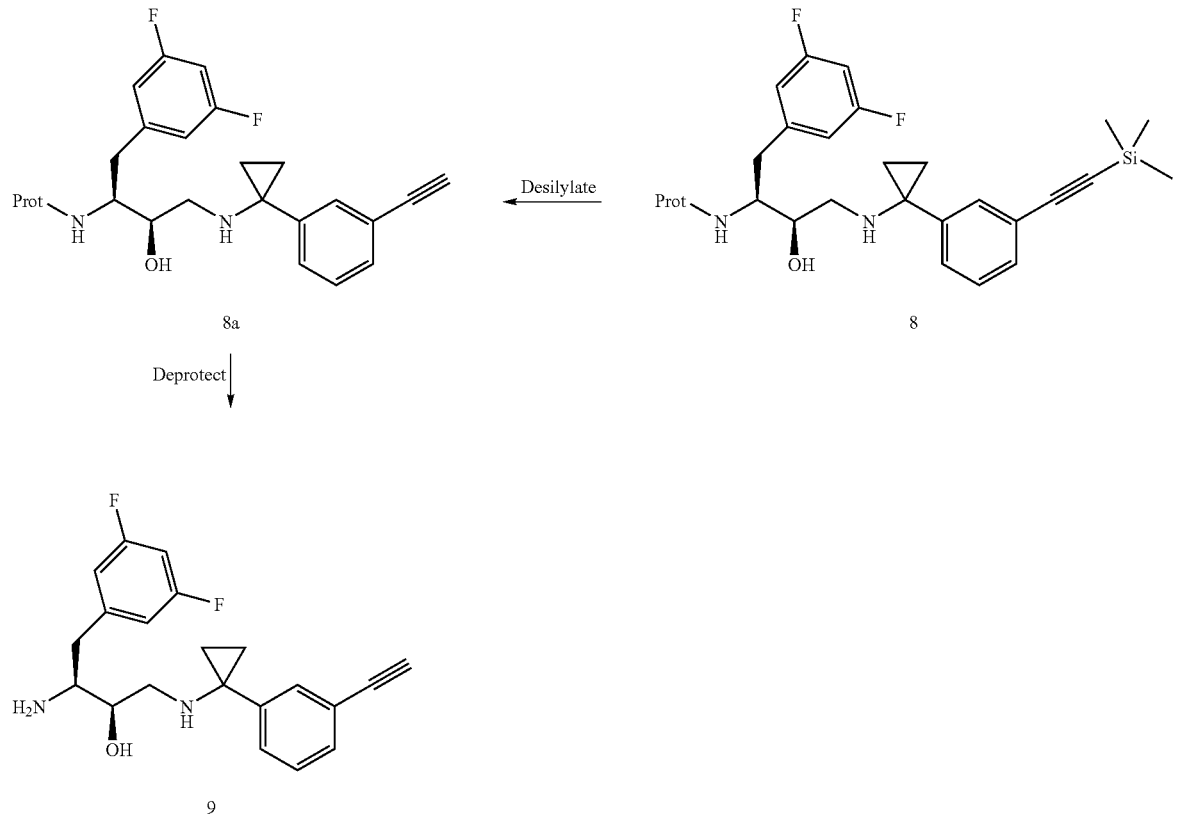
Scheme F
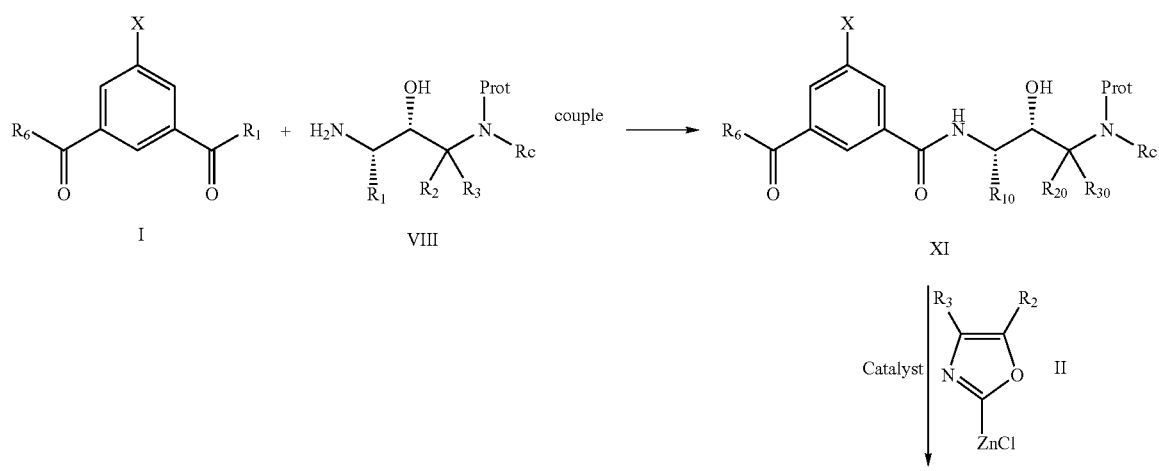

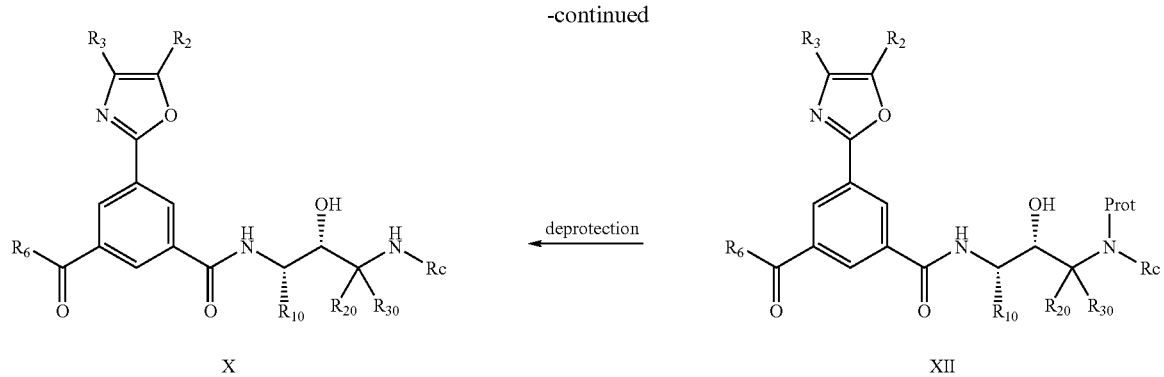

X                                                                 XII

The oxazolyl ester III can be used in situ or isolated. Those skilled in the art when trying to remove zinc salts often add acid so the zinc salts precipitate. Here if acid is added, the desired oxazolyl ester III will protonate and will also precipitate. Therefore, it is preferred to work-up the reaction by adding saturated ammonium chloride solution to the crude reaction mixture and extracting with a suitable organic solvent such as ethyl acetate. This work up method allows for the partition of the oxazolyl ester III into the organic phase with the zinc salts remaining in the aqueous phase.

Scheme A illustrates the preparation of the $ZnCl_2$/oxazole adduct. The scheme discloses the use of solid $ZnCl_2$. Solutions of $ZnCl_2$ can be used, but solid $ZnCl_2$ is preferred. The alkyllithium base used can be n-butyllithium t-butyllithium, sec-butyllithium, or methyllithium. N-butyl lithium is preferred. The lithiation of oxazoles has been described in Hodges, et al., *J. Org. Chem.* 1991, 56, 449; and Whitney, S. E., et al., *J. Org. Chem.* 1991, 56, 3058 and in references cited therein.

Scheme B illustrates a reaction between a compound of formula I (wherein $R_6$ is di-n-propylamine, X is Br, and $R_1$ is alkoxy) and a zinc chloride/oxazole adduct of formula II to form a coupled product of formula III. The ester is then hydrolyzed or otherwise cleaved to form the carboxylic acid.

Scheme C illustrates the conversion of a carboxylic acid of formula IV into an acid halide or an imidazolide (compound of formula V wherein $X_1$ is Cl or imidazolyl, respectively), or an acid anhydride (compound of formula VI). Scheme C further illustrates the coupling of the acid (IV), acid chloride (or bromide) (V), acid anhydride (VI) or imidazolide (V) with the amine of formula VIII to generate a compound of formula X. The amine and/or alcohol in compounds of formula VIII may be protected before the coupling reaction is performed. One of skill in the art can determine the need for the use of protecting groups. See for example, "Protective Groups in Organic Synthesis, third edition" by Wuts and Green. These couplings are also known to those of skill in the art. The coupled compounds of formula X are generally disclosed in International Publication WO 02/02512 based on PCT/US01/21012

International Publication WO02/02512 further discloses that the substituted amines of formula X are prepared by reacting the $R_N$ acid, acid halide, anhydride or carbonyl imidazole compound with the corresponding amine of formula VIII.

Schemes D and E disclose a method for preparing one possible amine of formula VIII.

Scheme F illustrates a coupling of a compound of formula I with an amine of formula VIII to form the amide of formula XI. In this scheme, it should be noted that the compound of formula I has not been coupled to the zinc chloride/oxazole adduct before being coupled to the amine of formula VIII. Compound XI can then be coupled to the zinc chloride/oxazole adduct to form compound XII. The protecting group can then be removed to form the compound of formula X.

All temperatures are in degrees Celsius.
CDI refers to 1,1'-carbonyldiimidazole.
MTBE refers to methyl t-butyl ether.
TLC refers to thin-layer chromatography.
HPLC refers to high pressure liquid chromatography.
Chromatography (column and flash chromatography) refers to purification/separation of compounds expressed as (support, eluent). It is understood that the appropriate fractions are pooled and concentrated to give the desired compound(s).
NMR refers to nuclear (proton) magnetic resonance spectroscopy, chemical shifts are reported in ppm (d) downfield from TMS.
CMR refers to C-13 magnetic resonance spectroscopy, chemical shifts are reported in ppm (δ) downfield from TMS.
MS refers to mass spectrometry expressed as m/e, m/z or mass/charge unit. [M+H]$^+$ refers to the positive ion of a parent plus a hydrogen atom. EI refers to electron impact. CI refers to chemical ionization. FAB refers to fast atom bombardment.
ESMS refers to electrospray mass spectrometry.
THF refers to tetrahydrofuran.
Ether refers to diethyl ether.
Saline refers to an aqueous saturated solution of sodium chloride.
Tetrakis(triphenylphosphine) Palladium refers to Pd(PPh$_3$)$_4$.
Pharmaceutically acceptable refers to those properties and/or substances which are acceptable to the manufacturing pharmaceutical chemist from a physical/chemical point of view regarding composition, formulation and stability.
When solvent pairs are used, the ratios of solvents used are volume/volume (v/v).
When the solubility of a solid in a solvent is used the ratio of the solid to the solvent is weight/volume (wt/v).
Dichlorobis(triphenyl-phosphine)palladium (II) refers to (PdCl$_2$(PPh$_3$)$_2$).
Triphenylphosphine oxide refers to Ph$_3$PO.
Prot refers to a protecting group or hydrogen. Protecting groups are well known to those skilled in the art. Further information on protecting groups can be found in, "Protective Groups in Organic Synthesis, third edition" by Wuts and Green.

Palladium(0) catalysts are those catalysts containing palladium with an oxidation state of zero. Palladium(0) catalysts include, but are not limited to: $Pd(PPh_3)_4$, $PdCl_2(PPh_3)_2$, $PdCl_2$, $PdCl_2$ and $PPh_3$, $Pd(OCOCH_3)_2$, and $((o\text{-Tol})_3P)_2PdCl_2$. One skilled in the art will recognize that some of the fore-mentioned palladium(0) catalysts contain palladium in an oxidized state, for example, $Pd(II)Cl_2$. One skilled in the art readily recognizes that the palladium(0) species can be generated in situ through the use of butyllithium, DIBAL-H or other reagents known in the art of organic synthesis. See for example, Negishi, et al., *J. Chem. Soc., Chem Commun.* 1986, 1338. The preferred palladium (0) catalyst is $Pd(PPh_3)_4$.

EXAMPLES

Starting materials are generally readily available from commercial sources, such as Sigma-Aldrich Corp. (St. Louis, Mo.), or may be prepared as described herein. The processes shown in the above schemes and set forth below in the Examples are not to be construed as limiting the invention in scope or spirit to the specific reagents and conditions shown in them. Those having skill in the art will recognize that the starting materials, reagents and conditions may be varied and additional steps employed in the processes of the invention and to produce compounds encompassed by the invention. In some cases, protection of reactive functionalities may be necessary to achieve the desired transformations. In general, such need for protecting groups, as well as the conditions necessary to attach and remove such groups, will be apparent to those skilled in the art of organic synthesis. Unless otherwise stated in the schemes below, the variables are as defined above.

All references mentioned in this application are incorporated by reference, in their entirety.

All reagents are of commercial grade unless otherwise noted. All reactions are stirred or otherwise agitated. Unless otherwise stated, none of the solvents were degassed.

Preparation 1 t-Butyl(1S,2R)-1-(3,5-difluorobenzyl)-3-{[1-(3-ethynylphenyl)cyclopropyl]amino}-2-hydroxypropylcarbamate Part (A)—Preparation of Bromophenylcyclopropylnitrile (2)

A mixture of 1-bromo-2-chloroethane (120 ml), 3-bromobenzyl cyanide (1, 25 g) and benzyl-triethylammonium chloride (1.1 g) is stirred at 40° while aqueous sodium hydroxide (50%, 120 g) is added dropwise over approximately 20 min. The reaction temperature rises to about 80° during the addition of the aqueous base. The reaction mixture is stirred very vigorous while the temperature slowly drops to 50° (over about 3 hr). After 3 hours, the reaction mixture is cooled down to 20–25°, water (100 ml) is added and the mixture stirred for 5 min. The organic phase is separated and the aqueous phase is extracted with dichloromethane (3×). The combined organic phases are washed with water and dilute hydrochloric acid. The organic phase is then dried over magnesium sulfate, filtered and concentrated. The concentrate is purified by a high vacuum fractionation using short-path set-up and single receiver. The fractions with bp=108–115°/0.1–0.05 mm Hg are collected; after cooling to 20–25° this liquid solidified.

Part (B)—Preparation of Bromoamide (3)

The bromophenylcyclopropylnitrile, ((2), part (A), 5.9 g; 26.6 mmol), is dissolved in methanol (150 ml). Potassium hydroxide (25% aqueous solution, 0.68 ml) and hydrogen peroxide (30%, 35 ml) are added and the reaction mixture is heated at 55° for 5 hr. The mixture is concentrated to give the crude bromoamide.

Part (C)—Preparation of Bromoacid (4)

The crude bromoamide ((3), part (B)) is slurried in methanol (10 ml) and sodium hydroxide (10% aqueous, 150 ml) is added. The reaction mixture is refluxed for 4.5 hr. The reaction mixture is then cooled to 20–25°, acidified to pH=2 with hydrochloric acid (15%) and concentrated. The resulting precipitated (6.8 g) is collected by filtration.

Part (D)—Preparation of Acid Chloride (5)

Thionyl chloride (2.73 ml) and benzotriazole (4.47 g) are dissolved in dry dichloromethane (25 ml.) 22.2 ml (1.25 equivalents) are then added portionwise over several minutes to the crude bromoacid ((4), part (C), 6.8 g) in dichloromethane (120 ml.) Before the addition is complete, benzotriazole hydrochloride started separating out as a white solid. The reaction mixture is stirred for an additional 15 min and then the solids are filtered off. The filtrate is stirred with anhydrous magnesium sulfate (2 g) to destroy an excess reagent. The solids are filtered off and the filtrate is concentrated under reduced pressure and dried under high vacuum for approximately 1 hr to afford the desired product (6.6 g.)

Part (E)—Preparation of Bromoamine (6)

The crude acid chloride ((5), part (D)), is dissolved in dry acetone (40 ml), cooled to −10° and treated with sodium azide (4 g in 15 ml of water). After stirring for 1 hr at −10° the mixture is allowed to warm to 0° and is poured into cold water (300 ml). The azide is extracted into smallest possible amount of toluene (about 40 ml). The toluene phase is separated and washed with water and dried over $Na_2SO_4$. The solids are filtered off and the filtrate is heated cautiously at 100° for 1 hr. Concentrated hydrochloric acid (about 25 ml) is added through the condenser and the mixture is refluxed for 15 min. On cooling a precipitate forms and is filtered off. The filtrate is slightly concentrated, cooled down and an additional portion of precipitate is collected. The combined solids are dried to give the desired product (4.1 g) as the hydrochloride salt.

Part (F)—Preparation of the 3,5-difluorobenzyl-bromo Compound (7)

The crude bromoamine ((6), part (E), 2 g; 8 mmol) is dissolved in saturated sodium carbonate (20 ml) and extracted with dichloromethane (5×10 ml). The combined extracts are dried, and concentrated. The extract containing the bromoamine (1.68 g, 7.92 mmol) is dissolved in isopropanol (20 ml) and BOC protected-3,5-difluorobenzylepoxide (ii, International Publication WO02/02512, EXAMPLE 3, 2.36 g, 7.92 mmol) is added. The mixture is heated to 80° in a sealed tube for 16 hours. The reaction mixture is concentrated to afford the crude 3,5-difluorobenzyl-bromo compound (3.9 g).

Part (G)—Preparation of Silyl Compound (8)

Crude 3,5-difluorobenzyl-bromo compound ((7), part (F), 3.9 g; 7.0 mmol; 1 equivalent) is dissolved in triethylamine (20 ml.) Dichlorobis(triphenyl-phosphine)palladium (II) (0.196 g, 0.28 mmol; 0.04 equivalents) and CuI (0.068 g; 0.36 mmol; 0.05 equivalents) are then added. The reaction mixture is heated to reflux and trimethylsilyl acetylene (0.82 g, 1.2 ml, 8.2 mmol, 1.2 equivalent) is added in one portion. The reaction mixture is refluxed for 3 hr under nitrogen, then it is cooled to 20–25° before partitioning between aqueous saturated sodium carbonate and ethyl acetate. The organic phase is separated and the aqueous phase is extracted with ethyl acetate (3×25 ml). The combined organic extracts are washed with brine, dried over $Na_2SO_4$, filtered and concentrated to give the desired silyl compound.

Part (H)—Preparation of BOC Protected-Acetylene Compound (8a)

Tetrabutylammonium fluoride (1M in THF, 8 ml) is added to a solution of the crude silyl compound ((8), part (G)) in THF (5 ml). The reaction mixture is stirred for 1 hr at 20–25° and then concentrated. The concentrate is dissolved in ether (30 ml), washed with brine, dried over $Na_2SO_4$, filtered, and concentrated. The crude product is purified by flash chromatography (silica gel; ethyl acetate/hexane, 2/3 mixture) to give the title compound.

Example 1

Methyl 1-[3-[(Dipropylamino)carbonyl]-5-(1,3-oxazol-2-yl)]benzoate

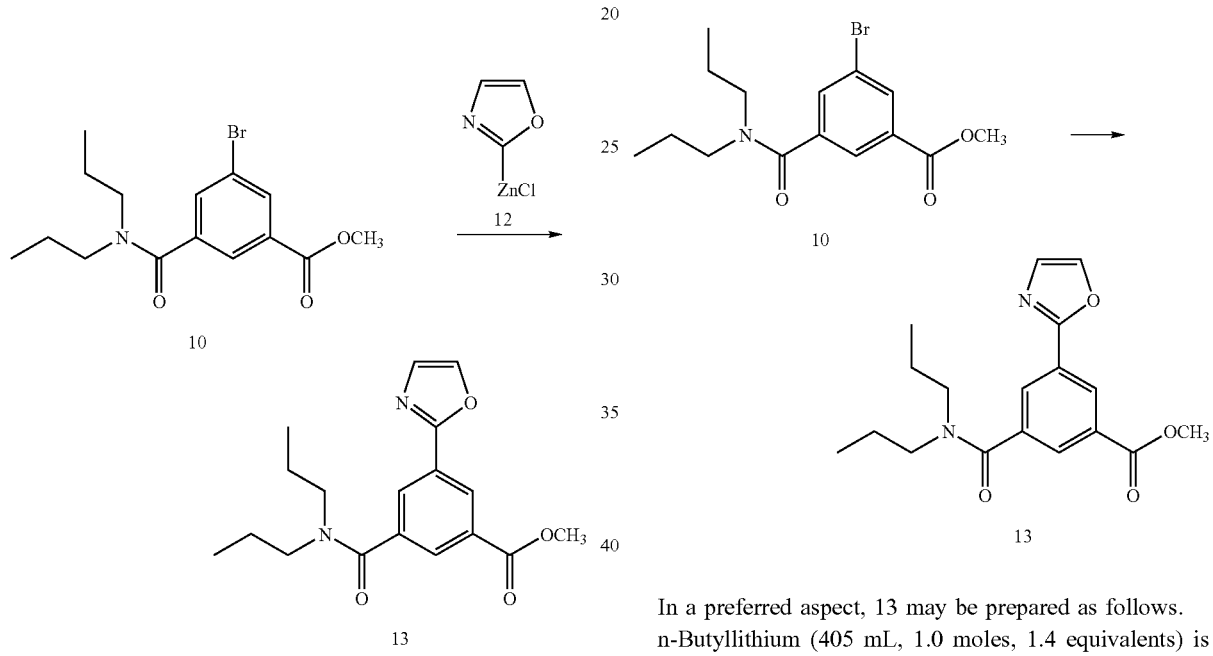

Compound 13 may be prepared as follows. n-Butyl lithium (1.4 equivalents) is added drop wise over 30 min to a stirred, −78° mixture of 1,3-oxazole (1.3 equivalents) in THF, while maintaining the mixture at a temperature below about −55° C. The mixture is stirred for 30 min and then solid zinc chloride (3 equivalents) is added in 3–10 portions over about 10–15 minutes. The cooling bath is then removed, the reaction mixture is allowed to warm to 20–25° and then the reaction is stirred for an additional 10 min. Next, the zinc chloride-oxazole adduct, 12, is added over a period of 2 hr to a mixture of methyl 3-bromo-5-[(dipropylamino)carbonyl]benzoate (10, WO02/02512, PREPARATION 3) and tetrakis(triphenylphosphine) palladium (5 mole %) in THF at 50°. Once the addition is complete, the reaction is stirred at 50° until no methyl 3-bromo-5-[(dipropylamino)carbonyl]benzoate 10 is observed by HPLC (usually about 1 hour.)

HPLC retention time=3.9 min (column: 15 cm luna phenylhexyl; acetonitrile/water, 0.2M ammonium formate; 65/35, λ=210 nm; 1.0 mL/min).

The reaction mixture is cooled to 20–25° and methyl t-butyl ether and hydrochloric acid (1N) are added. The phases are separated and the aqueous phase is extracted three times with methyl t-butyl ether. The combined organic phases are concentrated under reduced pressure to give a solid. The product is purified using silica gel chromatography (ethyl acetate/octane, 25/75 to ethyl acetate/octane 50/50) to give the title compound in 84% yield; NMR ($d_6$-DMSO) 8.50, 8.28, 8.10, 7.94, 7.44, 3.90, 3.38–3.14, 1.62–1.49 and 0.99–0.67 δ; CMR ($d_6$-DMSO) 168.56, 164.99, 159.29, 140.98, 138.77, 130.95, 128.41, 127.69, 126.53, 54.91, 52.67, 50.14, 45.93, 21.46, 20.27, 11.30 and 10.80 δ.

Example 2

Methyl 1-[3-[(dipropylamino)carbonyl]-5-(1,3-oxazol-2-yl)]benzoate

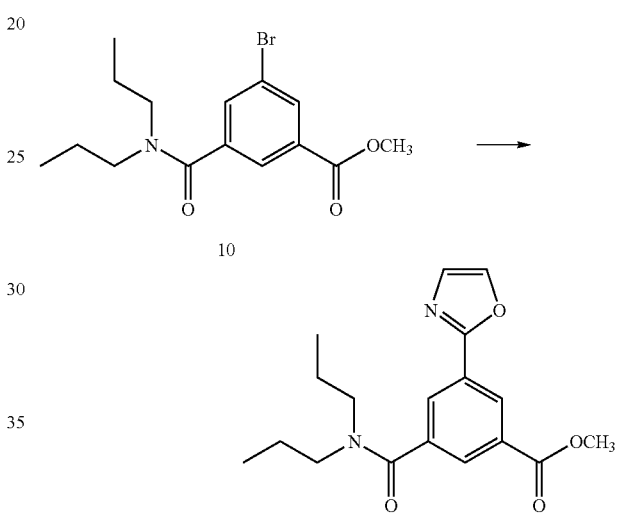

In a preferred aspect, 13 may be prepared as follows.

n-Butyllithium (405 mL, 1.0 moles, 1.4 equivalents) is added dropwise over approximately 30 min. to oxazole (50.32 g, 0.73 moles, 1.3 equivalents) in −78° THF, while maintaining the mixture at a temperature below about −55° C. Zinc chloride solid (300 g, 2.2 moles, 3 equivalents) is added in 3–10 portions over about 10–15 minutes and the reaction mixture is warmed to 20–25° by removing the cold bath.

Once at 20–25°, the reaction is stirred for an additional 10 min. and then methyl 3-bromo-5-[(dipropylamino)carbonyl] benzoate (10, 155 g, 0.45 moles, 1 equivalents) and tetrakis (triphenylphosphine) Palladium (5 mole %) are added. The reaction mixture is then heated to reflux and stirred until the starting material has been consumed. Once judged complete by HPLC, the reaction mixture is cooled to 20–25° and the crude reaction mixture is concentrated to dryness. To the resulting solid material is added $NH_4Cl$ and EtOAc. The phases are separated and the aqueous phase is extracted with ethyl acetate. The organic layers are combined and washed with saturated aqueous ammonium chloride. The solvent is removed under reduced pressure to give the title compound.

HPLC retention time=3.5 min (column: 15 cm luna phenylhexyl; acetonitrile/water, 60/40; λ=210 nm; 1.0 mL/min).

This material may be purified using silica gel chromatography (ethyl acetate/octane, 25/75 to ethyl acetate/octane 50/50) or be used without purification in the next step.

An alternative work up for the above reaction is as follows.

Once the reaction is complete, the reaction mixture is cooled to 20–25° C. and concentrated to afford a solid. EtOAc (1 L) and sat NH₄Cl (1 L) were added to the solid. The layers were separated and the aqueous layer was extracted with EtOAc (2×100 mL.) The combined organic layers were then washed with sat NH₄Cl (2×100 mL), and concentrated to afford the desired product.

Example 3

1-[3-[(Dipropylamino)carbonyl]-5-(1,3-oxazol-2-yl)] benzoic acid (14)

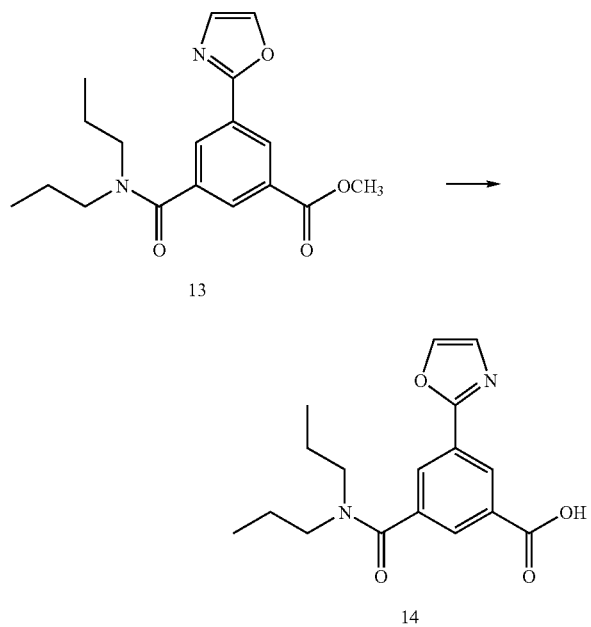

Aqueous sodium hydroxide (2N, 120 mL, 4 equivalents) is added portionwise to a mixture of methyl 1-[3-[(dipropylamino)carbonyl]-5-(1,3-oxazol-2-yl)]benzoate (13, EXAMPLE 2) in methanol (300 mL) at 20–25°. The resultant slurry is stirred at 20–25° for 1 hr at which time the reaction is judged to be complete by HPLC. Water is then added (3 volumes based on methanol), the layers are separated and the aqueous layer is extracted with MTBE until no triphenylphosphine oxide could be detected in the aqueous layer by HPLC. The pH of the aqueous layer is adjusted to less than one with concentrated hydrochloric acid and the product is extracted into ethyl acetate (200 mL). The ethyl acetate phase is separated and is subsequently distilled under reduced pressure while adding octane, which causes precipitation of the acid. The resulting solids are collected by filtration and dried under reduced pressure to give the title compound.

HPLC retention time=1.1 min (column: 15 cm luna phenylhexyl; acetonitrile/water; 60/40; λ=210 nm; 1.0 mL/min).

Example 4

(2R,3S)-3-amino-4-(3,5-difluorophenyl)-1-{[1-(3-ethynylphenyl)cyclopropyl]amino}butan-2-ol (17)

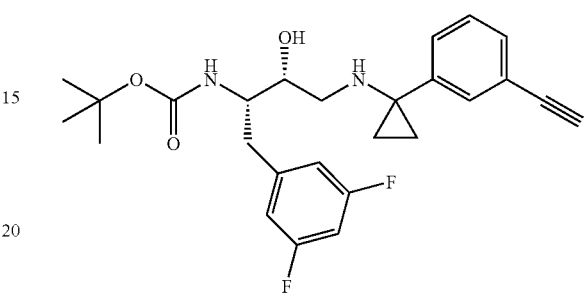

Acetyl chloride (84 mL, 1.18 moles, 15 equivalents based on the protected 3,5-difluorobenzyl compound) is added slowly to stirred methanol (250 mL). (Alternatively, HCl or TFA may be utilized.) The mixture is stirred for at least 15 min at which time t-butyl(1S,2R)-1-(3,5-difluorobenzyl)-3-{[1-(3-ethynylphenyl)cyclopropyl]amino}-2-hydroxypropylcarbamate (WO02/02512, PREPARATION 1, 37.8 g, 0.08 moles, 1 equivalent) dissolved in methanol (100 mL) is added slowly. The mixture is then stirred at 20–25° until the reaction is judged to be complete by HPLC. Once complete, the methanol is removed under reduced pressure and the resulting residue is dissolved in water (500 mL). This mixture is washed with MTBE (2×200 mL) and the combined organic phases are washed with hydrochloric acid (1N, 100 mL). The pH of the combined aqueous phases is adjusted to greater than 10 with base and then extracted with MTBE (2×200 mL). The combined organic phases are then concentrated to dryness under reduced pressure to give the title compound.

HPLC retention time=3.9 min (column: 15 cm luna phenylhexyl; acetonitrile/water, 0.2M ammonium formate; 65/35, λ=210 nm; 1.0 mL/min).

This product can then be dissolved in THF and used without purification in the coupling reaction.

Example 5

N¹-{(1S,2R)-1-(3,5-difluorobenzyl)-3-[(3-ethylbenzyl)amino]-2-hydroxypropyl}-5-(1,3-oxazol-2-yl)-N³,N³-dipropylisophthalamide (19)

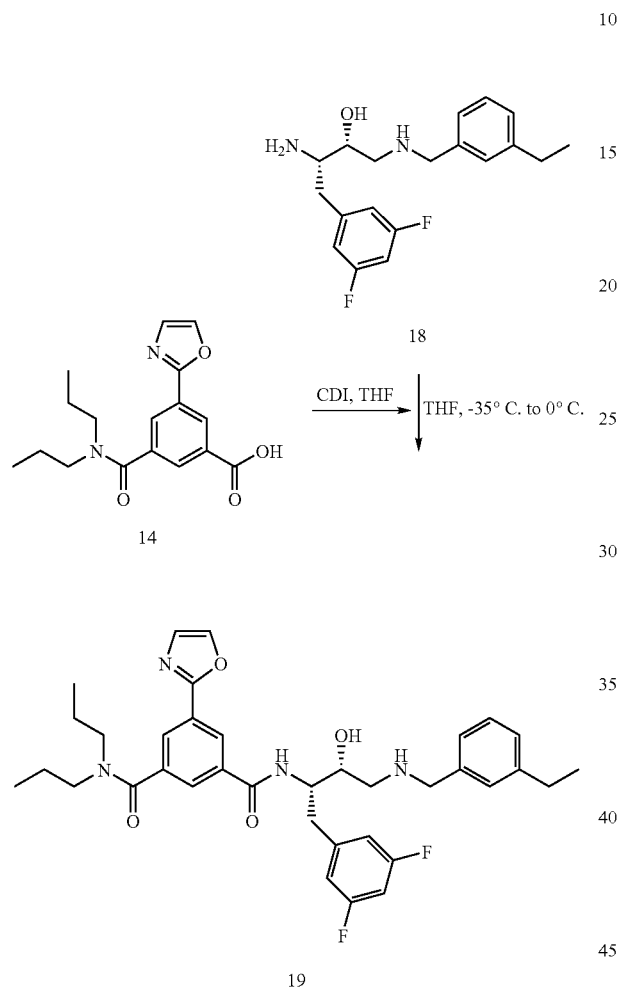

Solid 1-[3-[(dipropylamino)carbonyl]-5-(1,3-oxazol-2-yl)]benzoic acid (14, EXAMPLE 3, 1.0 equivalents) is added slowly to CDI (1.3 equivalents) in room temperature THF. The resulting mixture is stirred for at least 1 hr at which time it is added slowly over 1 hr to a −35° mixture of (2R,3S)-3-amino-4-(3,5-difluorophenyl)-1-[(3-ethylbenzyl)amino]butan-2-ol (18, International Publication WO02/02512, 1.0 equivalent) in THF. After this addition, the reaction is warmed to 0° and stirred until complete by HPLC. Once judged complete, the contents are poured into hydrochloric acid (1N) and the aqueous phase is separated and extracted with ethyl acetate. The combined organic phases are washed with saturated sodium bicarbonate and the solvent removed under reduced pressure. The crude product is purified using silica gel chromatography to afford the title compound.

Example 6

N¹-((1S,2R)-1-(3,5-difluorobenzyl)-3-{[1-(3-ethynylphenyl)cyclopropyl]amino}-2-hydroxypropyl)-5-(1,3-oxazol-2-yl)-N³,N³-dipropylisophthalamide (20)

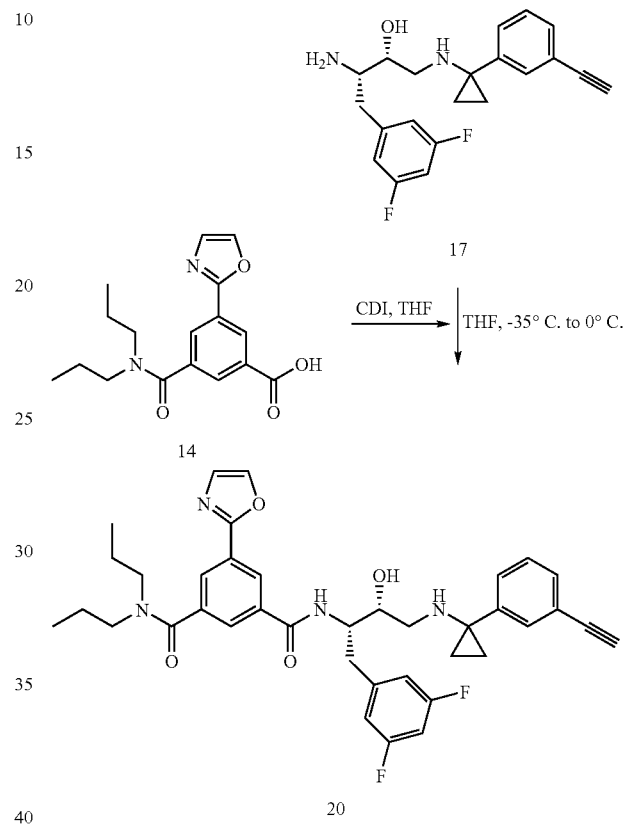

Solid 1-[3-[(Dipropylamino)carbonyl]-5-(1,3-oxazol-2-yl)]benzoic acid (14, EXAMPLE 3, 23 g, 0.08 moles, 1.0 equivalent is added slowly to a mixture of CDI (14.6 g, 0.09 moles, 1.3 equivalents) in THF (150 mL). The resultant mixture is stirred at 20–25° for at least 1 hr at which time it is added slowly over 1 hr to a −35° mixture of (2R,3S)-3-amino-4-(3,5-difluorophenyl)-1-{[1-(3-ethynylphenyl)cyclopropyl]amino}butan-2-ol (17, EXAMPLE 4, 28 g, 0.08 moles, 1.0 equivalent) in THF (300 mL). After this addition is complete, the reaction is allowed to warm to 0°. Once judged complete, the reaction mixture is poured into hydrochloric acid (1N, 500 mL.) The aqueous phase is then separated and extracted with ethyl acetate (2×500 mL). The combined organic extracts are washed with saturated sodium bicarbonate (250 mL) and then concentrated. The crude product is purified using silica gel chromatography to afford the title compound.

HPLC retention time=4.7 min (column: 15 cm luna phenyl-hexyl, acetonitrile/water, 0.2 ammonium formate, 65/35, λ=210 nm, 1.0 mL/min).

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

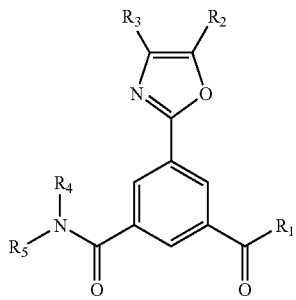

wherein:

$R_1$ is OH, halogen, $C_1$–$C_4$ alkoxy, —OC(O)CH$_3$, or —OC(O)CF$_3$;

$R_2$ and $R_3$ are independently H or $C_1$–$C_4$ alkyl; and $R_4$ and $R_5$ are independently $C_1$–$C_6$ alkyl.

2. A compound according to claim 1, wherein $R_2$ and $R_3$ are independently H or methyl.

3. A compound according to claim 2, wherein $R_4$ and $R_5$ are both $C_3$ alkyl.

4. A compound according to claim 3, wherein $R_1$ is OH.

5. A compound according to claim 3, wherein $R_1$ is $C_1$–$C_4$ alkoxy.

6. A compound according to claim 3, wherein $R_1$ is chloro.

7. The compound according to claim 4 which is 3-(dipropylcarbamoyl)-5-(oxazol-2-yl) benzoic acid.

8. The compound according to claim 5 which is Methyl 3-(dipropylcarbamoyl)-5-(oxazol-2-yl)benzoate.

* * * * *